United States Patent [19]

Miyazawa et al.

[11] Patent Number: 4,879,223

[45] Date of Patent: Nov. 7, 1989

[54] METHOD FOR PRODUCING PROTEIN CONTAINING NONPROTEIN AMINO ACIDS

[75] Inventors: Tatsuo Miyazawa; Shigeyuki Yokoyama, both of Bunkyo; Tetsuo Miyake, Koda, all of Japan

[73] Assignee: Wakunaga Seiyaku Kabushiki Kaisha, Osaka, Japan

[21] Appl. No.: 186,075

[22] Filed: Apr. 25, 1988

[30] Foreign Application Priority Data

Apr. 24, 1987 [JP] Japan ................................ 62-101581

[51] Int. Cl.$^4$ ............................................. C12P 21/00
[52] U.S. Cl. ..................................................... 435/68
[58] Field of Search ..................................... 435/68–70, 435/172.3, 320

[56] References Cited

U.S. PATENT DOCUMENTS

| 2,180,637 | 11/1939 | Kemmerer | 435/68 |
| 4,119,493 | 10/1978 | Isowa | 435/70 |
| 4,568,640 | 2/1986 | Rubin | 435/70 |

OTHER PUBLICATIONS

Brown & Otros, "4–Fluorotryptophan Alkaline Phosphatase From *E. coli*," Biochemical & Biophysical Research Communications, vol. 68, No. 3, pp. 907–913 (1976).

Hagen, Weiner and Sykes, "Fluorotyrosine M13 Coat Protein," Biochemistry, vol. 17, No. 18, pp. 3860–3866 (1978).

Sykes, Weingarten & Schlesinger "Fluorotyrosine Alkaline Phosphatase from *Escherichia coli*," Proc. Nat., Acad. Sci., vol. 71, No. 2, pp. 469–473 (1974).

Wilson Hatfield, "Incorporation of Modified Amino Acids into Proteins In Vivo", Biochimica et Biophysica Acta, vol. 781, pp. 205–215 (1984).

*Primary Examiner*—Peter D. Rosenberg
*Attorney, Agent, or Firm*—Wenderoth, Lind & Ponack

[57] ABSTRACT

A protein having nonprotein amino acids can be produced by a method which comprises providing a protein-producing organism with a nutrient containing nonprotein amino acids, cells being cultured to produce the protein in a medium containing the nonprotein amino acids, in which method expression of a gene coding for the protein is induced under conditions in which normal cell growth is suppressed.

9 Claims, 3 Drawing Sheets

METHOD FOR PRODUCING PROTEIN CONTAINING NONPROTEIN AMINO ACIDS

BACKGROUND OF THE INVENTION

1. Field of the Invention

The present invention relates to a method for producing proteins comprising nonprotein amino acids or alloproteins. From another view point, the present invention relates to a method for substituting a part of amino acids comprising a given protein by nonprotein amino acids.

2. Prior Art

It is being appreciated according to disclosures in numerous literature, specifications of patent publications or the like that a technology for producing desired gene products in abundance is on the way to be established by means of DNA recombination techniques. Furthermore, by addition of appropriate manipulations to a base sequence of a desired foreign gene, it has become possible to partially change an amino acid sequence or an amino acid composition of a desired natural protein. Consequently, the usefulness and effectiveness of desired gene products are enhanced. Additionally, proteins whose natural amino acids or protein amino acids have been artificially replaced can serve as materials, for example, for investigations of structure-activity correlations or mechanisms of biological functions. Thus, a method for producing such proteins will contribute immensely to both industrial and academic fields.

However, as long as the gene manipulation techniques mentioned above are to be used, all amino acids constituting a resultant gene product must be selected restrictively from 20 natural amino acids, namely glycine, alanine, valine, leucine, isoleucine, serine, threonine, aspartic acid, glutamic acid, asparagine, glutamine, lysine, arginine, cysteine, methionine, phenylalanine, tyrosine, tryptophan, histidine and proline. In other words, it is impossible to produce a protein which comprises nonprotein amino acids.

On the other hand, another method for producing proteins is that by chemical synthesis. Recently, techniques of chemical synthesis have been rapidly advanced so that it has become possible to synthesize long chain peptides using this method. According to this method, it is not at all difficult to synthesize peptides containing various nonprotein amino acids. However, it is substantially impossible to provide such long chain peptides using this method in an abundant amount for industrial and academic uses since the yield markedly decreases generally with extension of the chain length.

Therefore, development of a method for producing proteins containing nonprotein amino acids is now being expectantly hoped for.

SUMMARY OF THE INVENTION

An object of the present invention is to solve the foregoing problems and, more specifically, to solve the problems by providing a method i which a nutrient source containing nonprotein amino acid is given to a protein-producing organism under a certain specified condition and a protein that the organism has produced which comprises the nonprotein amino acid fed is then recovered.

Accordingly, the present invention relates to the improvement in a method wherein an organism capable of producing a protein is provided with a nutrient source containing a nonprotein amino acid whereby a protein comprising the nonprotein amino acid copolymerized therein is produced, which improvement comprising subjecting the organism which is being provided with the nutrient source to conditions such that normal growth of the organism or the protein synthesis associated with the growth is suppressed.

In accordance with the present invention, it becomes possible to produce entirely new proteins which have nonprotein amino acids as well as natural amino acids as constituent amino acids, the proteins that may be called alloproteins.

Such alloproteins are useful in view of a variety of utilizations as will be mentioned later.

Cells of microorganisms, when cultured, synthesize indigenous proteins (naturally, natural proteins) from sources of carbon, nitrogen and sulfur on the basis of endogenous genetic information. We have found that microorganisms efficiently produce through biosynthesis proteins comprising nonprotein amino acids copolymerized therewith, even when the nonprotein amino acids are greatly different in properties from amino acids for natural proteins, namely viz. natural amino acids, if microorganisms are cultured in a medium containing the nonprotein amino acids under a certain specified condition. This is regarded as an interesting phenomenon.

In this connection, in the production of proteins by organisms, it is a natural phenomenon as it is or a generally practiced technology that nutrient sources containing natural amino acids are used to supply amino acids for constructing the proteins. In the case where a nutrient source contains nonprotein amino acids, known so far are those in which the amino acids are added merely for purposes mainly of interfering protein synthesis [Biochimica et Biophysica Acta 781, 205 (1984); Trends in Biochemical Sciences, 320 (Sept. 1983)], or those in which the amino acids used are exclusively nontoxic to host cells and yet incorporated without altering functions of proteins [Proc. Natl. Acad. Sci. USA 71, 469 (1974); Biochem. Biophys. Res. Commun. 68, 907 (1976); Biochemistry 17, 3860 (1978); Proc. Natl. Acad. Sci. USA 78, 2707 (1981)].

On the contrary, the nonprotein amino acids according to the present invention are supplied under a specified condition for purposes of efficiently producing proteins which comprise the nonprotein amino acids. The present invention is thus based on a finding which is unexpected even to those skilled in the art.

DETAILED DESCRIPTION OF THE INVENTION

Production of non-natural proteins

Figure 1:
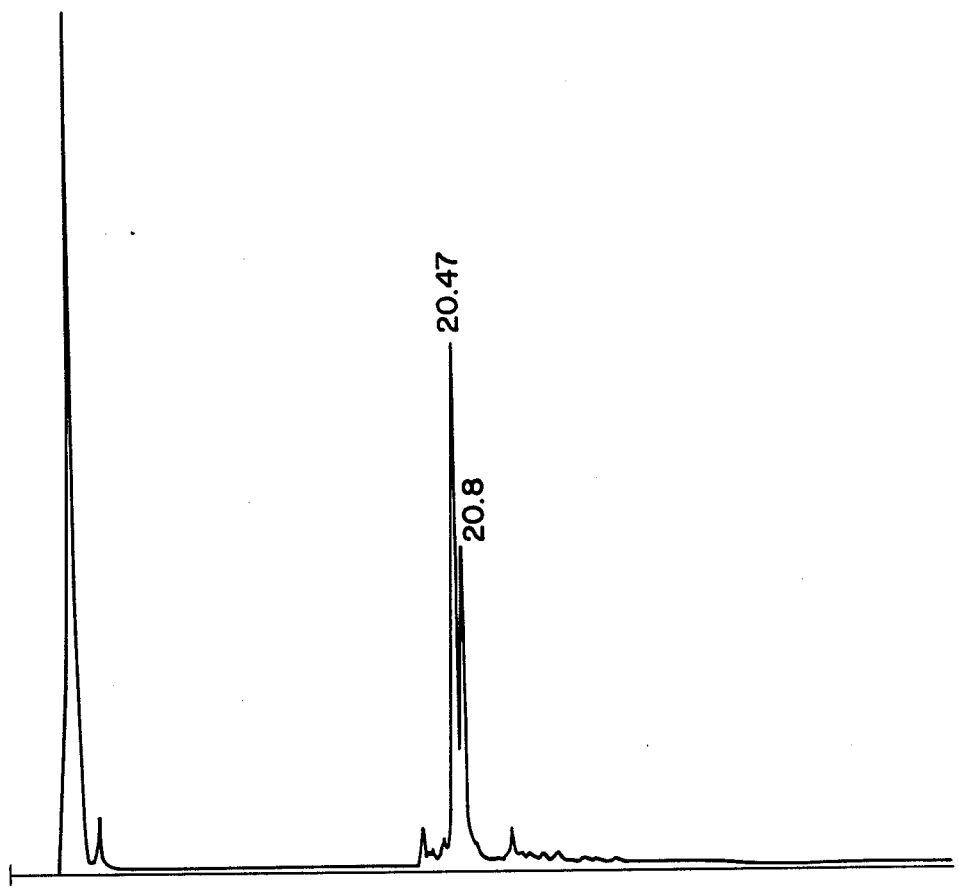
FIGS. 1 and 2 are reproductions of chromatograms of HPLC chromatography.

The present invention relates to a method for producing proteins comprising nonprotein amino acids (hereinafter referred to as non-natural proteins) using protein-producing organisms.

The term "nonprotein amino acids" as used herein implicates all amino acids excluding the aforementioned 20 natural amino acids. Thus, all amino acids but the aforementioned 20 amino acids are referred to as nonprotein amino acids even if they are naturally present. The term "organisms" as used herein implicates, besides cells of animals and plants, the animals and plants themselves. Representatives of these organisms are cells of animals and plants and microbial cells. Furthermore, "proteins" to be produced embrace all those generally defined as proteins and also those with combinations with sugar chains, namely, glycoproteins.

Accordingly, hormones, enzymes and many others as well as so-called protein fibers are also embraced. Of these proteins, well-known examples are insulin, interferons, growth hormones, serum albumin and epidermal growth factor.

The present invention is based on a finding that nonprotein amino acids can be recognized by aminoacyl-tRNA synthetase and, after binding to corresponding tRNAs, incorporated into a system for protein synthesis in an organism so that a protein comprising the nonprotein amino acids is produced. Accordingly, in order to incorporate nonprotein amino acids into a desired protein and then to recover efficiently, in the case where organisms employed are, for example, cells of microorganisms, it is advantageous to use recombinants which have been transformed by means of gene manipulation so as to produce the protein in high yield. Methods for producing these recombinants are known in the art.

In the case where a protein is synthesized by incorporation of such nonprotein amino acids into cells of a host organism, it is advantageous to induce the expression of a structural gene for a desired protein under the condition that growth of the host cells be suppressed or more precisely, that new synthesis of proteins essential for ordinary physiology of the host cells be suppressed.

In the case where nonprotein amino acids to be incorporated into a desired protein are not toxic to a host, the incorporation can be achieved simply by adding corresponding nonprotein amino acids to a culture medium. In this case, if a mutagen strain which requires corresponding amino acids is employed as a host, efficiency of incorporation can be set as desired by changing the ratio of the nonprotein amino acids to corresponding natural or protein amino acids in the medium.

In the case where nonprotein amino acids are toxic to a host or act lethally, it is impossible to substitute these nonprotein amino acids with corresponding amino acids of a desired protein. In this case, however, under the condition that host growth is suppressed, the toxicity of nonprotein amino acids is decreased to some extent so that protein synthesis may be continued (J. Biol. Chem. 244, 3810 (1969)). It is, therefore, essential to suppress new synthesis of proteins essential for ordinary physiology of the host cells to induce the expression of a structural gene of the desired protein.

In practice, nonprotein amino acids are added to a medium in the stationary phase of bacterial growth. More particularly, by using a mutant strain of bacteria which requires corresponding amino acids to be replaced, the bacterial cells are grown to produce a certain bacterial count in a medium containing a minimum amount of corresponding natural amino acids, and thereafter the medium is replaced by a medium supplemented with a predetermined amount of the desired nonprotein amino acids. Alternatively, the cells are grown in a medium of high phosphate concentration, and thereafter the medium is replaced by a medium of low phosphate concentration. In this case, the appropriate promoter for a structural gene to be expressed is one derived from alkaline phosphatase. Furthermore, similar effect can be achieved by inducing the expression in the stationary phase of bacterial growth by the use of promoter/operator regulation systems comprising, for example, the trp promoter, the tac promoter or the ;ar promoter, for inducible gene expression, which is widely used in the field of producing substances by gene manipulation. On the other hand, in the case where a promoter derived from a heat shock protein is used, syntheses of host proteins can be suppressed by means of heat shock. In this case, it is preferable to use as an expression vector a runaway type plasmid which increases the number of copies with a rise in temperature. It is also preferable to reduce the amino acid concentration in a medium, release the gene expression, which is suppressed by stringent control, and then induce the expression of the objective structural gene by using a non-stringent promoter.

In the modification of a desired protein, depending on the purpose, the following methods can be applied to the nonprotein amino acids to be incorporated.

(1) Method using nonprotein amino acids as they are

In the case where the environment for protein synthesis differs from that for usage of an objective protein, the difference can be advantageously used. For example, a pyridylalanine residue is neutral in an environment of protein synthesis to be incorporated into a protein as a substrate of phenylalanyl tRNA synthetase, but when the objective protein is used in an acidic environment, the residue is positively charged with an addition of protons.

(2) Method using nonprotein amino acids as precursors so as to utilize metabolisms in organisms For example, an indole derivative is added to a medium and then introduced into cells so as to produce a tryptophan derivative, which is incorporated into a protein as it is.

(3) Method altering a protein comprising nonprotein amino acids after recovery to a desired protein derivative by a treatment such as oxidation, reduction or hydrolysis For example, the following treatments are carried out.

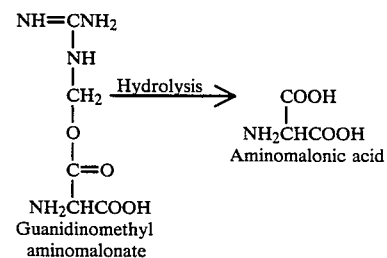

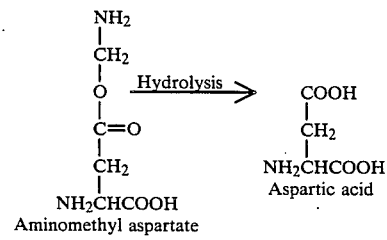

There may be a variety of nonprotein amino acids to be added to a medium according to the present invention. Representative examples among them are as follows:

(a) Nonprotein amino acids which are modifications of natural amino acids in that imino groups or divalent non-carbon atoms such as oxygen or sulfur of the natural amino acids have been substituted by methylene groups, or, alternatively, amino groups, hydroxyl groups or thiol groups have been substituted by methyl groups, so as to eliminate their capability of forming hydrogen bonds or to enhance their hydrophobic property;

Example:
Methionine→Norleucine (b) Nonprotein amino acids which are modifications of natural amino acids in that methylene groups of the natural amino acids have been substituted by imino groups or divalent non-carbon atoms or, alternatively, methyl groups have been substituted by amino groups, hydroxyl groups or thiol groups, so as to add capability of forming hydrogen bonds or to reduce hydrophobic property;

Examples
Lysine→S-2-Aminoethylcysteine
Isoleucine→O-methylthreonine (c) Nonprotein amino acids which are modifications of natural amino acids in that methylene group or methyl groups have been added to the natural amino acids so as to enhance hydrophobic property;

Examples:
Leucine→γ-methylleucine
Valine→β-methylvaline (t-Leucine)

(d) Nonprotein amino acids which are modifications of natural amino acids in that methylene groups or methyl groups of the natural amino acids have been removed to reduce hydrophobic property;

Example:
Isoleucine→Norvaline (e) Nonprotein amino acids which are modifications of natural amino acids in that amino groups, hydroxyl groups or thiol groups of the natural amino acids have been removed or methylated so as to eliminate capability of forming hydrogen bonds;

Examples:
Threonine→O-methylthreonine
Lysine→Norleucine (f) Optical isomers regarding side chains of natural amino acids;

Example:
Isoleucine→Alloisoleucine (g) Nonprotein amino acids which are modifications of natural amino acids in that substituent groups have been introduced as side chains to the natural amino acids;

Example:
Asparagine→β-fluoroasparagine (h) Nonprotein amino acids which are modifications of natural amino acids in that atoms of aromatic side chains of the natural amino acids have been replaced so as to change hydrophobic property, electrical charge, fluorescent spectrum or reactivity;

Examples:
Phenylalanine→Pyridylalanine
Tyrosine→p-Aminophenylalanine (i) Nonprotein amino acids which are modifications of natural amino acids in that rings of aromatic side chains of the natural amino acids have been expanded or opened so as to change hydrophobic property, electrical charge, fluorescent spectrum or reactivity;

Examples:
Phenylalanine→Naphthylalanine
Phenylalanine→Pyrenylalanine (j) Nonprotein amino acids which are modifications of the natural amino acids in that side chains of the natural amino acids have been oxidized or reduced so as to add or remove double bonds;

Examples:
Alanine→Dehydroalanine
Isoleucine→Beta-methylenenorvaline (k) Nonprotein amino acids which are modifications of proline in that the five-membered ring of proline has been opened or additionally substituent groups have been introduced therein;

Example:
Proline→N-methylalanine (l) Nonprotein amino acids which are modifications of natural amino acids in that the second substituent group has been introduced at the α-position;

Example:
Lysine→α-difluoromethyllysine (m) Nonprotein amino acids which are combinations of one or more of different or same alterations used in the (a)-(l); and Example:
Tyrosine→p-Methoxy-m-hydroxyphenylalanine (n) Nonprotein amino acids which differ in chemical structures from natural amino acids but can serve as substrates for aminoacyl tRNA synthetase by assuming conformation analogous to natural amino acids when bound to this enzyme.

Example:
Isoleucine→Furanomycin

Cells to be cultured in a medium containing such nonprotein amino acids may be any suitable ones which produce proteins, the term "protein" herein including glycoproteins.

Such cells may be either wild type cells or transformants, the term "transformants" herein including products by transfection and transduction. Consequently, proteins to be produced by the cells according to the present invention can be those which wild-type cells cannot produce. In view of diversity of non-natural proteins with nonprotein amino acids incorporated, or alloproteins, the proteins to be produced by the cells are preferably different from those produced by wild type cells. In other words, it is preferable that the cells to be used in the present invention be transformants.

Representative cells according to the present invention are those of *Escherichia coli* and transformants thereof, and an example of the protein to be produced is a human epidermal growth factor (hereinafter referred to as EGF).

Non-natural Proteins

As mentioned above, according to the present invention, it is now possible to create entirely new proteins, or alloproteins, in which nonprotein amino acids as well as 20 natural amino acids are used as constituents.

By the use of such proteins, it becomes possible to prepare functional drugs, antagonistic drugs or inhibitory agents. Also, by the use of amino acids other than and in addition to 20 natural ones in protein engineering, potentialities of designs of proteins are enormously extended. Since such alloproteins are non-natural, they are not easily decomposed by proteolytic enzymes generally present in cells of organisms.

In the case where alloproteins are synthesized to which have been introduced at specified positions nonprotein amino acids having chemically highly active functional groups at side chains thereof, various types of site-specific modifications are possible by the use of reactivities of the functional groups introduced. For example, it may be possible to produce proteins which have undergone site-specific phosphorylation, methylation or addition of sugar chains. It may be possible to produce alloproteins as derivatives analogous to specified proteins by the introduction of nonprotein amino acids having functional groups to form crosslinkages so that cellular components which interact with the specified proteins in the cells can be detected. Alloproteins with incorporations of fluorescent amino acid residues are useful to trace metabolic pathways in organisms or to elucidate mechanisms of biological actions. It is possible to produce alloproteins with introductions of nonprotein amino acids which differ in acid dissociation constant from natural amino acids, so as to control activities of the proteins depending on acidity in aqueous solutions.

Thus, alloproteins can be widely utilized in the investigation of the structure and function of proteins. On the basis of the findings thus obtained, the way for designing of new useful alloproteins will be opened up.

It is possible to introduce nonprotein amino acids into proteins having the capability of self-assembling such as viruses (e.g., coat proteins), muscle fibers (e.g., actin and myosin) or chromatin (e.g., histones) so as to create supra-molecular structures having specified functions. Alternatively, supra-molecular structures can be created by the use of capability of biological cells in constructing structures.

It may be possible to add nonprotein amino acids according to the present invention to artificial feeds for silk worms so as to synthesize silk with the nonprotein amino acids incorporated therein. It may be possible to produce durably colored protein fibers from alloproteins to which colored amino acids have been incorporated. Furthermore, it may be possible to introduce into neoproteins nonprotein amino acids having functional groups to form crosslinkages, for example, so as to produce supra-molecular structures with silk as supporting construction. Crosslinkages of the protein fibers then result in producing new proteinous resins. Into the structures thus produced, nonprotein fluorescent amino acids are introduced to make biochips for photoenergy transduction.

EXPERIMENTAL EXAMPLES

Example 1

Preparation of 21-Norleucine EGF

Cells of *E. coli* YK537 (pTA1522) were pre-cultured in Luria Broth and then cultured as taught in Japanese Patent Laid-Open Publication No. 61-37099 in 2.4 lit. of TG+20 medium containing 40 mg/lit. leucine, 40 mg/lit. thiamine and 40 mg/lit. ampicillin at 37° C. overnight with shaking. The collected cells were suspended in 2.4 lit. of TG+1 medium containing leucine, thiamine, ampicillin and norleucine at concentrations of 0.2 to 4 g/lit., individually, and then further cultured at 37° C. for 6 hours. Subsequently, the periplasm fraction was recovered according to the method disclosed in Japanese Patent Laid-Open Publication No.61-37099 and then fractionated on a Sephadex G-50 column (medium, $\Phi$2.6 cm×100 cm, 25 mM $CH_3COONH_4$, pH 5.8) to recover a fraction which reacts with EGF antiserum.

In this connection, the strain "*E. coli* YK537 (pTA1522)" is constructed by introduction of plasmid pTA1522 into "*E. coli* K12YK537" as deposited under the deposition number FERM BP-822, and the plasmid pTA1522 in turn is inducible according to the method disclosed in Japanese Patent Laid-Open Publications Nos. 60-30687 and 61-37099 from *E. coli* K12C600 (pYK283) as deposited under the deposition number FERM BP-556, the deposits FERM BP-822 and FERM BP-556 being international deposits deposited at Fermentation Research Institute, Japan, under the Budapest Treaty.

Purification

Figure 2:
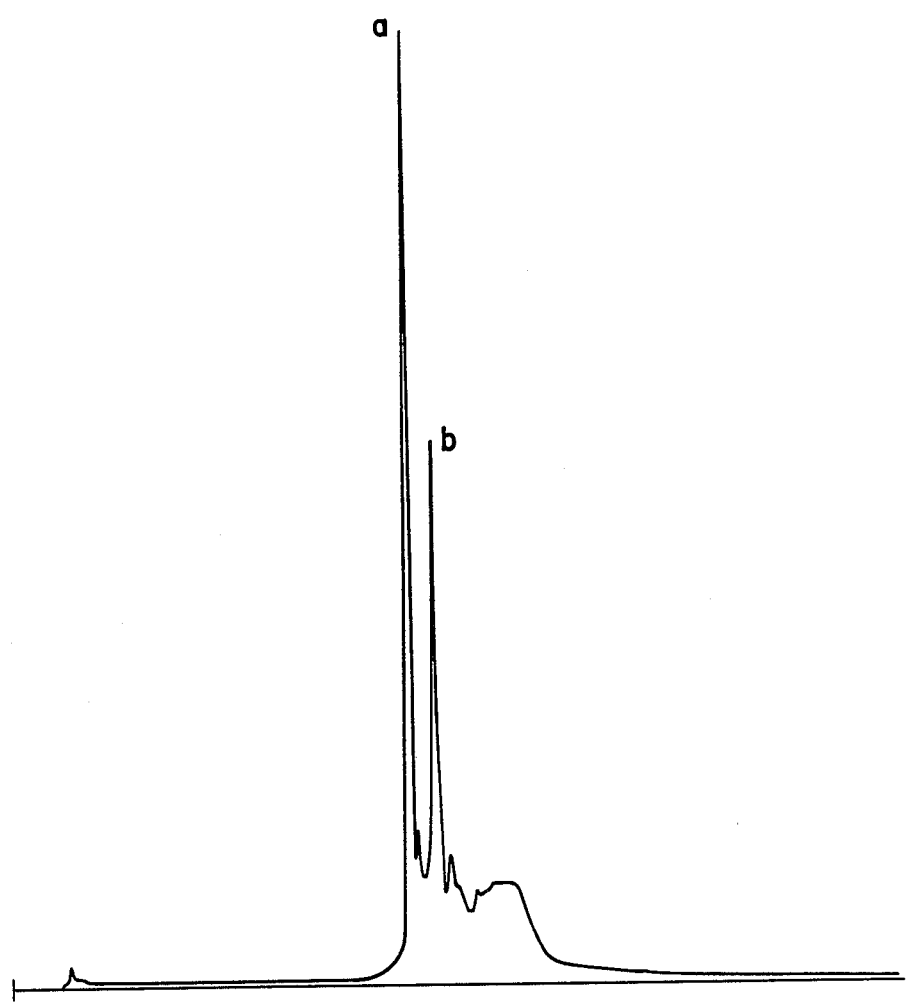

An active fraction recovered from the Sephadex G-50 column was introduced onto reverse-phase HPLC ODS-120T (TOSOH, $\Phi$ 4.6 mm×25 cm) and eluted with a concentration gradient (flow rate, 1 ml/min) from 20% to 40% acetonitrile in 0.1% TFA (trifluoroacetic acid). Besides a peak of EGF (at 20.47 minutes), a new peak at 20.8 minutes was recognized (FIG. 1). Separation of the two peaks was difficult, so that the fractions from the two peaks were combined and treated with 0.3% $H_2O_2$ at room temperature for 30 minutes to oxidize methionine residues of EGF and then again purified on HPLC under the same conditions to obtain two fractions, peak a (at 19.52 minutes) and peak b (at 20.64 minutes) as shown in FIG. 2.

Confirmation of 21-Norleucine-EGF

Figure 3:
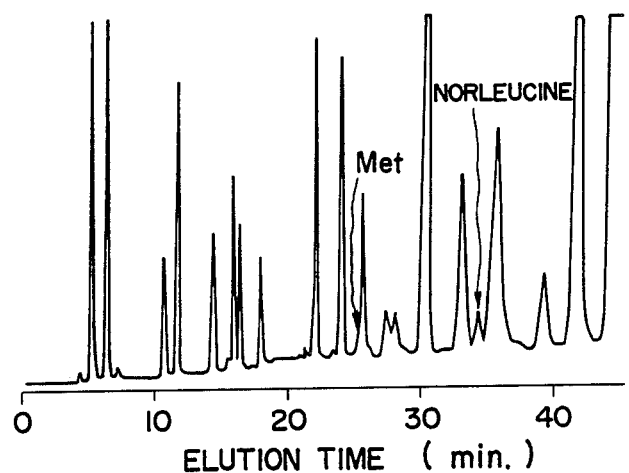
FIGS. 3 to 6 are graphs each showing the result of amino acid analysis of norleucine-EGF, canavanine-EGF, p-fluorophenylalanine-EGF and pyridylalanine-EGF.

According to the conventional method, the fraction of the peak b was treated with 6N HCl-1% phenol at 115° C. for 24 hours to hydrolyze and subjected to amino acid analysis with an H-type standard sample containing norleucine. According to the analysis, norleucine was detected, but methionine was not detected (FIG. 3). This fraction exhibited reactivity with EGF anti-serum similar to EGF and furthermore, exhibited an analogy with EGF in activity to introduce thymidine measured by RRA method with EGF and KB cells or by using 3T3 cells (Japanese Patent Laid-Open Publication No. 61-37099).

The results mentioned above indicate that the protein thus obtained and derived from the peak b is an EGF derivative in which methionine residues of EGF are substituted by norleucine residues.

EXAMPLE 2

Preparation of EGF Derivative Containing Canavanine

Figure 4:
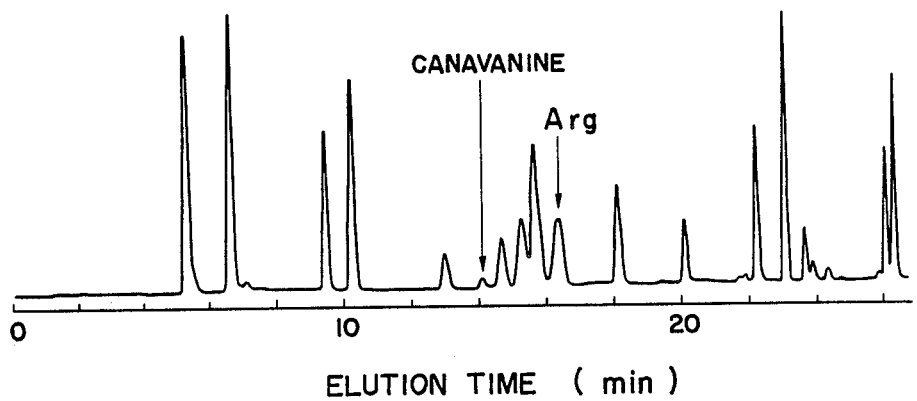

Canavanine is a nonprotein amino acid lethal to cells. Cells of an *E. coli* strain (carrying plasmid pTA1522) which requires arginine were incubated in TG+1 medium containing 50 mg/lit. of the nonprotein amino acid and then subjected to fractionation in the same manner as in Example 1. After gel filtration an EGF fraction was purified by reverse-phase HPLC. Amino acid analysis revealed that an EGF derivative containing canavanine copolymerized therein was produced (FIG. 4).

EXAMPLE 3

Preparation of EGF Derivative Containing p-Fluorophenylalanine

Figure 5:
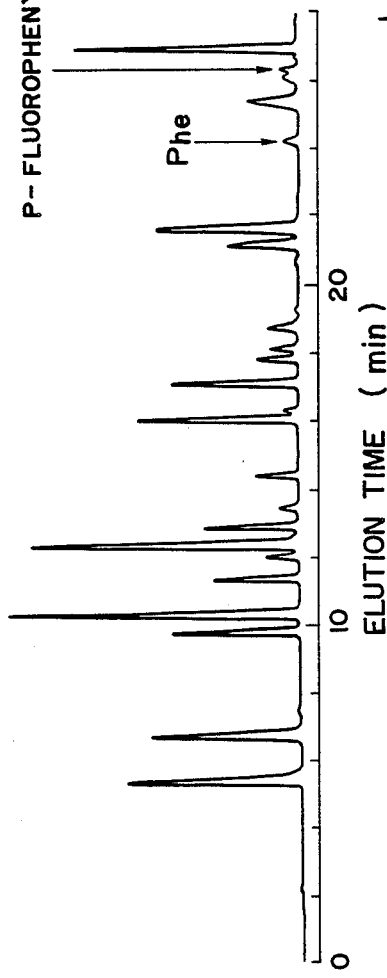

Plasmid pTA152-29F was prepared by inducing a site-directed mutation in EGF gene to replace the 29th Tyr of EGF with Phe. This plasmid was introduced into a *E. coli* strain which requires phenylalanine and then cells of the *E. coli* were cultured in TG+1 medium containing 50 mg/lit. of p-fluorophenylalanine and then subjected to fractionation in the same manner as in Example 1. After gel filtration an EGF fraction was purified by reverse-phase HPLC. Amino acid analysis revealed that an EGF derivative containing p-fluorophenylalanine copolymerized therein was produced (FIG. 5).

EXAMPLE 4

Preparation of EGF Derivative Containing Pyridylalanine

Figure 6:
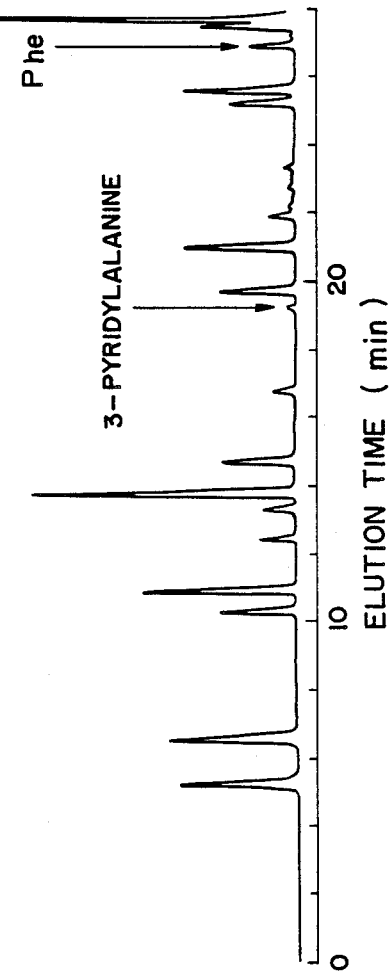

Cells of the aforementioned *E. coli* carrying plasmid pTA152-29F were cultured in TG+1 medium containing 50 mg/lit. of pyridylalanine and then subjected to fractionation in the same manner as in Example 1. After gel filtration an EGF fraction was purified by reverse-phase HPLC. Amino acid analysis revealed that an EGF derivative containing pyridylalanine copolymerized therein was produced (FIG. 6).

EXAMPLE 5

Preparation of Other EGF Derivatives Containing Nonprotein Amino Acids

Cells were cultured in TG+1 media containing nonprotein amino acids, namely, S-2-aminoethylcystein, O-methylthreonine, norvaline, γ-methylleucine, β-methylvaline and α-difluoromethyllysine, at concentrations of 50–300 mg/lit. and treated in the same manner as described above to purify individual EGF fractions using reverse-phase HPLC after gel filtration. As a result, new peaks as shown in FIG. 1 were obtained. Amino acid analysis revealed that each of the fractions was an EGF derivative containing the nonprotein amino acids copolymerized therein.

What is claimed is:

1. In a method wherein an organism capable of producing a protein is provided with a nutrient source containing a nonprotein amino acid whereby a protein comprising the nonprotein amino acid copolymerized therein is produced, the improvement which comprises subjecting the organism to conditions such that growth of the organism or the protein synthesis associated with the growth is suppressed, the suppression being such that it takes place even when the nutrient source is free from the nonprotein amino acid.

2. A method as set forth in claim 1, wherein expression of a gene coding for a foreign protein is induced under the conditions that growth of the organism or the protein synthesis associated with the growth is suppressed.

3. A method as set forth in claim 2, which comprises a step of culturing cells of the organism in a medium containing the nonprotein amino acid.

4. A method as set forth in claim 3, wherein said cells are those of a microorganism.

5. A method as set forth in claim 2, wherein the growth of an organism or the protein synthesis associated with the growth is suppressed by the control of a phosphate concentration in the culture medium used.

6. A method as set forth in claim 2, wherein the gene coding for the protein has an expression promoter derived from the alkaline phosphatase operon.

7. A method as set forth in claim 2, wherein said protein is an epidermal growth factor.

8. A method as set forth in claim 2, wherein said nonprotein amino acid is selected from the group consisting of the following members (a) to (n):

(a) Nonprotein amino acids which are modifications of natural amino acids in that imino groups or divalent non-carbon atoms sellected from the group of oxygen and sulfur of the natural amino acids have been substituted by methylene groups, or, alternatively, amino groups, hydroxyl groups or thiol groups have been substituted by methyl groups, so as to eliminate their capability of forming hydrogen bonds or to enhance their hydrophobic property;

(b) Nonprotein amino acids which are modifications of natural amino acids in that methylene groups of the natural amino acids have been substituted by imino groups or divalent non-carbon atoms or, alternatively, methyl groups have been substituted by amino groups, hydroxyl groups or thiol groups, so as to add capability of forming hydrogen bonds or to reduce hydrophobic property;

(c) Nonprotein amino acids which are modifications of natural amino acids in that methylene groups or methyl groups have been added to the natural amino acids so as to enhance hydrophobic property;

(d) Nonprotein amino acids which are modifications of natural amino acids in that methylene groups or methyl groups of the natural amino acids have been removed to reduce hydrophobic property;

(e) Nonprotein amino acids which are modifications of natural amino acids in that amino groups, hydroxyl groups or thiol groups of the natural amino acids have been removed or methylated so as to eliminate capability of forming hydrogen bonds;

(f) Optical isomers regarding side chains of natural amino acids;

(g) Nonprotein amino acids which are modifications of natural amino acids in that substituent groups have been introduced as side chains to the natural amino acids;

(h) Nonprotein amino acids which are modifications of natural amino acids in that atoms of aromatic side chains of the natural amino acids have been replaced so as to change hydrophobic property, electrical charge, fluorescent spectrum or reactivity;

(i) Nonprotein amino acids which are modifications of natural amino acids in that rings of aromatic side chains of the natural amino acids have been expanded or opened so as to change hydrophobic property, electrical charge, fluorescent spectrum or reactivity;

(j) Nonprotein amino acids which are modifications of the natural amino acids in that side chains of the natural amino acids have been oxidized or reduced so as to add or remove double bonds;

(k) Nonprotein amino acids which are modifications of proline in that the five-membered ring of proline has been opened or additionally substituent groups have been introduced therein;

(l) Nonprotein amino acids which are modifications of the natural amino acids in that the second substituent groups have been introduced at the α-positions;
(m) Nonprotein amino acids which are combinations of one or more of different or same alterations used in the (a)–(l); and
(n) Nonprotein amino acids which differ in chemical structures from natural amino acids but can serve as substrates for aminoacyl tRNA synthetase by assuming conformation analogous to natural amino acids when bound to this enzyme.

9. A method as set forth in claim 4, wherein the microorganism is *Escherichia coli*.

* * * * *